United States Patent [19]

Urbascheck et al.

[11] Patent Number: 4,663,298

[45] Date of Patent: May 5, 1987

[54] METHOD FOR DETERMINING ENDOTOXIN CONCENTRATIONS

[76] Inventors: Bernhard Urbascheck; Klaus-Peter Becker; Bernhard Ditter, all of c/o Abt. für Immunologie und Serologie am Inst. für Hyg. und Med. Mikrobiol. Fakultät für Klinische Med. Mannheim der Universität Heidelberg D 6, 5, 6800 Mannheim, Fed. Rep. of Germany

[21] Appl. No.: 691,007

[22] Filed: Jan. 14, 1985

[30] Foreign Application Priority Data

Oct. 31, 1984 [DE] Fed. Rep. of Germany ....... 3439761

[51] Int. Cl.$^4$ ........................................... G01N 33/579
[52] U.S. Cl. ....................................... 436/502; 435/4; 435/23; 436/517
[58] Field of Search ............... 436/175, 502, 825, 517; 435/4, 23

[56] References Cited

U.S. PATENT DOCUMENTS 4,273,557 6/1981 Jurands ............................. 436/502
4,376,819 3/1983 Brown ............................. 436/502 X

OTHER PUBLICATIONS

H. A. Flaschka et al., "Quantitative Analytical Chemistry", 2nd Edition, pp. 435, 454, 455, Willard Grant Press, Boston, Mass., 1980.

*Primary Examiner*—Sidney Marantz
*Attorney, Agent, or Firm*—Wegner & Bretschneider

[57] ABSTRACT

The method for determining endotoxin concentrations in samples and, if present, interfering factors by adding defined amounts of endotoxin to the sample and computational evaluation of the reaction kinetics can be improved by adding, to at least two identical preparations of a sample, different amounts of endotoxin. These endotoxin amounts, however, are at least ten times the amount of the endotoxin to be determined in the sample. By determining a regression line as the reference curve from the measured values, the endotoxin amount of a preparation of the sample to which no endotoxin has been added is determined. The effect caused by interfering factors and the endotoxin neutralization capacity can be determined from the slope and position of the regression line. The absorbance in a turbidimetric measurement may be enhanced by using a small amount of a chromogenic substrate whereby a reduction in the amount of the sample preparation to be assayed will be possible.

4 Claims, 5 Drawing Figures

FIG. 5

Internal Standardization

| Example No. | Type | $\Delta OD_{max}$/minute (Samples spiked with endotoxin) | | | $\Delta OD_{max}$/minute (Samples without spike) | Slope of individual standard curve (interference factor) | Endotoxin concentration in the sample (EU/ml) |
|---|---|---|---|---|---|---|---|
| | | spike (EU/ml) 1 | 10 | 100 | | | |
| 1 | water | 8.0 | 11.5 | 14.7 | 0 | 3.3 | 0 |
| 2 | CSF | 0.9 | 14.1 | 18.3 | 4.8 | 4.2 | 0.06 |
| 3 | plasma (heated) | 32.0 | 43.3 | 55.1 | 19.8 | 11.6 | 0.09 |
| 4 | plasma (unheated) | 3.5 | 17.0 | 31.1 | 0 | 13.8 | neutralization capacity: 0.6 EU/ml |

METHOD FOR DETERMINING ENDOTOXIN CONCENTRATIONS

BACKGROUND OF THE INVENTION

The present invention relates to a method for determining endotoxin concentrations in samples and, if present, potentially interfering factors.

The inventors have already described such a method based on the addition of defined amounts of endotoxin to a sample and computational evaluation of the reaction kinetics; cf. Arzneimittel-Forschung 33 (I), 5, 681–687 (1983) Editio Cantor. The method is based on the known fact that the lysate of the amoebocytes from the hemolymph of the horseshoe crab (Limulus polyphemus; Tachypleus tridentatus et al.) forms a gel in the presence of endotoxins. This gel-forming reaction proceeds via an enzyme chain of which not all steps have been elucidated. This basic principle for the detection of endotoxin is used, for example, in the semi-quantitative tube gelation test (clot test), the turbidimetric endpoint or two-point determination and various methods for assaying the Limulus Amoeboctye Lysate-Endotoxin (LAL-ET) reaction kinetics.

In the conventional quantitative methods it is required to investigate several sample dilutions because of the narrowly limited range of measurement. In addition thereto, erroneous determinations may occur, more particularly in testing substances which will interfere with the detection reaction. So far it has not been possible to obtain insight into the behavior of a sample as to type and extent of said interference and, at the same time, to determine the endotoxin content thereof.

According to inventor's aforementioned publication, in a very meticulous and expensive procedure increasing amounts of a standardized endotoxin were added to preparations of the sample to be tested, and the reaction kinetics were determined by means of a quantitative turbidimetric LAL microtiter test. Typical examples of such reaction kinetics have been shown in FIG. 1 of the publication. The maximum increase in the optical density per minute vs. the logarithm of the endotoxin concentration provides an endotoxin standard curve which is linear throughout an extremely large range. Such a typical endotoxin standard curve comprising a range of from 8 to 4,000 pg/ml is shown in FIG. 2 of the publication.

Furthermore, reaction profiles were determined with constant spikes of endotoxin by assaying sample dilutions comprising constant endotoxin spikes. Depending on the tested sample these reaction profiles resulted in an inhibition, enhancement or in the absence of interfering factors. Such typical reaction profiles are shown in FIG. 3 of the publication.

Frequently, the determination of unknown amounts of endotoxins is significantly affected by interfering factors. Thus, reliable results so far have only been obtainable if, upon investigation and evaluation of the reaction kinetics, an internal standardization has been determined by means of an elaborate mathematical computation in accordance with a non-linear model.

SUMMARY OF THE INVENTION

It is the objective of the present invention to develop a simplified and improved method for determining endotoxin concentrations in samples and, if present, interfering factors. Then, such a method also would be suitable to be employed as a routine procedure in clinical practice, the pharmaceutical industry and in research; it follows that the results as obtained thereby could be put into diagnostic, differential-diagnostic, therapeutical and prognostic use as well as applying it in the in-process and final checking procedures as well as in experimental studies.

This object and others are obtained through the present invention. This invention provides a method for the determination of endotoxin concentrations in samples and, if present, of interfering factors. This method involves adding of different amounts of endotoxin to at least one identical preparations of a sample. These amounts, however, are at least ten times the amount of the endotoxin to be determined in the sample. A regression line is drawn as the reference curve from the measured values. From this regression line the endotoxin amount of a preparation of the sample to which no endotoxin has been added is determined .

It is preferred that three or four identical preparations of a sample are spiked to different degrees with ten to one thousand times the amount of the supposed endotoxin concentration and the regression line is determined from the measured values. In this case, the amount of endotoxin in the sample can be determined from the preparation to which no endotoxin has been added without disturbances caused by interfering factors.

By using this invention, it is further possible to determine the effects caused by the interfering factors and the endotoxin neutralization capacity from the slope and position of the regression line obtained from an optionally pre-treated preparation of the sample in comparison to the regression line obtained from water or a standard solution. For example, in testing non-treated plasma samples and plasma samples that were heated for a period of time, it was observed that the endotoxin neutralization capacity present in the non-heated plasma is eliminated by heating. Instead, an enhancement of the reaction is generally observed. Furthermore, it was observed that the endotoxin neutralization capacity in the plasma is subject to considerable variation. The observations as hitherto made suggest that a low endotoxin neutralization capacity or a drop of this parameter is to be considered as an alarm signal. An increased endotoxin neutralization capacity or the increase thereof in the course of repeated determinations can be viewed positively with respect to prognosis. The variation in slopes of the regression lines which indicates enhancing or inhibiting factors could not yet be differential-diagnostically evaluated. However, there is some evidence that highly deviating slopes of the regression lines also indicate particular conditions of the patients. The combined consideration of the endotoxin concentration in relationship to the interference and the endotoxin neutralization capacity in the course of a disease may provide additional confirmation of the ratings given to the individual parameters.

DETAILED DESCRIPTION

The method provided by this invention allows determination of the endotoxin content, as well as possibly present potentially interfering factors, in a substantially easier and less expensive manner with considerably reduced computational expenditure.

With the prior state of the art, it has either been possible to obtain inaccurate and unreliable results at a reasonable expenditure or to obtain more accurate and reliable results at a high expenditure which is unacceptable for practical routine. Thus, it was indeed surprising that with this invention it is possible to obtain reliable results with a significantly reduced input of work, material and equipment.

The measurement of the endotoxin concentrations according to the invention may be carried out in a per se known manner by turbidimetry or by photometry using chromogenic substrates. It has been found that with this invention it is also possible to add only a small amount of a chromogenic substrate and then to measure the sum of turbidity and color absorption. Namely, it has been observed that large amounts of a chromogenic substrate act to inhibit the enzyme system of the lysate, and that there also is a risk that an additional amount of endotoxin is introduced into the sample together with the chromogenic substrate. With the addition of a relatively small amount of a chromogenic substrate, this risk will be lower, while higher absorbencies can be measured. While maintaining accuracy, this enables one to use smaller volumes of samples and reagents. Smaller volumes in turn will save sample material, lysate and other reagents.

For carrying out the method according to the invention, commercially available lysates are used which are selected on the basis of sensitivity as required. Using the method according to the present invention, higher sensitivities than those declared by the producers are generally achieved. More detailed tests on the commercially available lysates have resulted in the finding that lower concentrations may be employed. Thereby, 50 to 75% of lysate per preparation can be saved.

Pyrogen-free water (LAL negative) or suitable buffer solutions are used for the reconstitution of the lysate and for all endotoxin standard and sample dilutions.

As the standard endotoxin, commercially available endotoxins may be used, e.g. EC-5 (FDA) and NP1 (Hermalchemie).

As the chromogenic substrate, all substrates which are capable of reacting with the key enzyme amidase and being pyrogen-free may be used (e.g. Kabi or Pentapharm). The substrate concentrations to be employed (e.g. 0.02 mMol/1) are less than one tenth to a fortieth of the concentrations as required for conventional two-point measurements for the endotoxin determination.

As the sample, any material may be employed that is soluble in water or in the aforementioned buffer solutions or may be rinsed by using these. When testing protein-containing samples, a short-term heat treatment (70° C. to 95° C.; 1 to 15 minutes) or some other pretreatment such as dilution, pH shifting, extraction, precipitation, etc. may be employed.

For receiving the reaction preparations, commercially available microtiter plates that have proven to be pyrogen-free are preferred to be used.

For monitoring the reaction kinetics, any photometer may be used in which the microtiter plate may be held at a pre-determined temperature during the measuring period and which allows a sequence of measurements to be conducted with a period of 5 minutes or less, depending on the reaction rate in the preparations. For the turbidimetric measurements, light having a wave length preferably of between 300 and 405 nm is used. When using chromogenic substrates, the measurement is preferably carried out at the absorption maximum.

For measurement control, data transfer and evaluation of the measurement, computers are suitable which can be coupled with the photometer.

In general, the amounts used for the reaction are between 50 $\mu$l and 200 $\mu$l. A volume of 100 $\mu$l is preferred, which is composed of 50 $\mu$l of the sample or the standard, respectively, 25 $\mu$l of water or endotoxin spike, and 25 $\mu$l of the reconstituted lysate.

When measurements employing a chromogenic substrate are carried out, each reaction preparation additionally contains a constant amount of said substrate. Dependent on the possibility to precisely handle small volumes and to analyze these photometrically, the volumes to be employed may be reduced. Additional chromogenic substrate may be used to cause a sufficient increase in the optical density.

In order to establish the standard curves, defined endotoxin concentrations and amounts of lysate in suitable ratios are mixed. The endotoxin concentrations are selected to be adapted to the case of application and the sensitivity of the lysate is chosen so that the concentrations in the preparations will be in the range between the sensitivity limit of the lysate and a value of up to 100,000 pg/ml. For example, a standard curve having been measured over the range of from 0.5 pg/ml to 8,200 pg/ml will be suitable for routine analyses. The sample to be tested is pretreated if required and/or desired and then mixed in a suitable ratio with the lysate. Two to four preparations containing different endotoxin spikes which are in excess of the expected endotoxin content of the sample by at least 1 or 2 orders of magnitude, and one or two preparations without endotoxin spikes added are employed. The smallest endotoxin spike added should amount to at least ten times the approximate amount of endotoxin expected to be determined in the sample. The preparations are preferably selected so that they are enriched by spikes of from ten to one thousand times the amount of endotoxin present in the sample.

For determining the endotoxin neutralization capacity (also denoted as the critical endotoxin concentration), in the same manner an unpre-treated sample is investigated by means of addition of highly excessive amounts of endotoxin.

After the reactions of each preparation have been initiated by the addition of the lysate, the optical density of each preparation is measured and recorded during the period of measurement in intervals that are sufficiently small such as to enable the subsequent evaluation to be made. Dependent on the reaction rates, the intervals are to be selected from between 5 minutes and 5 seconds. One minute intervals have been found to be useful for routine determinations.

From the recordings that have been obtained by using this method, the maximal increase in optical density per time unit ($\Delta OD_{max}$/min) was determined for each preparation by evaluating the individually measured values, in accordance with prior art methods. As a substitute for the quick computation of the differences of each of two subsequently measured values, which yields less precise results, methods were already used which cause the smoothing of measured values. The methods employed were (a) calculating an average increase over several measured values;

(b) adaptation of the steep slope section of the reaction kinetics by a polynomial of the first to the third order;

(c) adaptation of the entire reaction kinetics by nonlinear functions, such as, e.g. the Gomperts function. Also, the time at which the maximal increase occurred ($t(\Delta OD_{max})$), the total increase in optical density (plateau, $\Delta OD_{tot}$), and the time of beginning increase of the reaction kinetics ($t_{on}$) were determined for use in the subsequent evaluations.

The comparative investigation of different lysates provided information on the kinetics, sensitivity limits, contamination and endotoxin-independent background reaction of the lysate and, hence, allows the employed lysates to be assessed.

The data as determined for the maximal increase in the optical density of the standard preparations were transformed by using mathematical functions. Additionally the values for the time of occurrence of the maximal increase and the values for the total increase in optical density can be used. The values obtained by said transformation, in relation to the known endotoxin concentrations of the respective standard preparations, provided a linear standard curve extending over at least four logs. The selection of the transformation was determined depending on the lysate, the desired measurement range, and the photometer, all of which together determine the form of the reaction kinetics as measured. For photometers having a vertical rays path and comprising measurement ranges distinctly higher than the sensitivity limit of the lysate, e.g., it is suitable to plot the maximal velocity of increase over the logarithm of the endotoxin concentration of the standard. In measurements which approach the sensitivity limit of the lysate, the use of the root of the maximal velocity of increase resulted in a linear standard curve. A reduction of the relative interference factor was accomplished by using the quotient ($\Delta OD_{max}/\min)/(\Delta OD_{tot}$).

From the standard curves, which were obtained with the transformation of the values measured for individual preparations in the same manner, the transformed values of said preparations could be read directly, and the endotoxin content could be calculated directly.

In the endotoxin assay according to the two-point or endpoint method, the increase in optical density of the preparations was measured within a pre-determined period of time depending on the endotoxin content. Different measurement ranges in which a linear standard curve was obtained were found depending on the time of reading. The correlation of the required reading time to the desired measurement range was possible due to the analysis of the reaction kinetics of the preparations of a standard curve over a wide range.

From the results as already published by the inventors and obtained by using the very elaborate analytical technique, it was already known that substances causing an inhibition or an enhancement of the endotoxin-lysate reaction are abundantly found. Thus, the methods having been published by other authors will only yield correct results, if it has been ascertained that such an interference of the sample with the detecting reaction does not occur. However, a sample-internal standardization in the form of a non-linear model is subject to such high computational expenditure that routine tests in practice will hardly be possible therewith.

With this invention, it has been determined that it also is possible to obtain good and reliable results at substantially less expenditure. Moreover, these results may even be obtained by using smaller computers. The cross-checking of said results by using the much more elaborate, previously published method lead to the conclusion that the results are achieved by the method according to the present invention are fully satisfactory and reliable.

Data as determined by the method according to the invention may be utilized in the investigation of plasma samples, in which in the course of a disease not only differing endotoxin concentrations, but also significantly different endotoxin neutralization capacities and interferences were measured. Increasing endotoxin concentrations and decreasing endotoxin neutralization capacities apparently can be considered as an alarm signal indicating that further differential-diagnostic and therapeutical measures will be necessary. On the other hand, low endotoxin concentrations and high endotoxin neutralization capacities can be considered to justify termination of intensive care treatment.

In addition, the method according to the present invention also provides the determination of the endotoxin concentrations in a fast and reliable way making it applicable in other fields, e.g. in the production of solutions for injection and/or infusion, the production of antibiotics, etc. For example, by the method according to the present invention it can be determined in a very simple manner whether the material to be tested contains interfering factors or has endotoxin neutralization capacity, which using previous methods for determining provided false-negative results, or whether the materials to be tested may be readily tested in accordance with conventional methods as well. Furthermore, in accordance with the present invention it will be possible to abandon at least part of the animal experiments having so far been required for the detection of endotoxin.

The invention is explained in greater detail by way of the following Examples and Figures.

Figure 1:
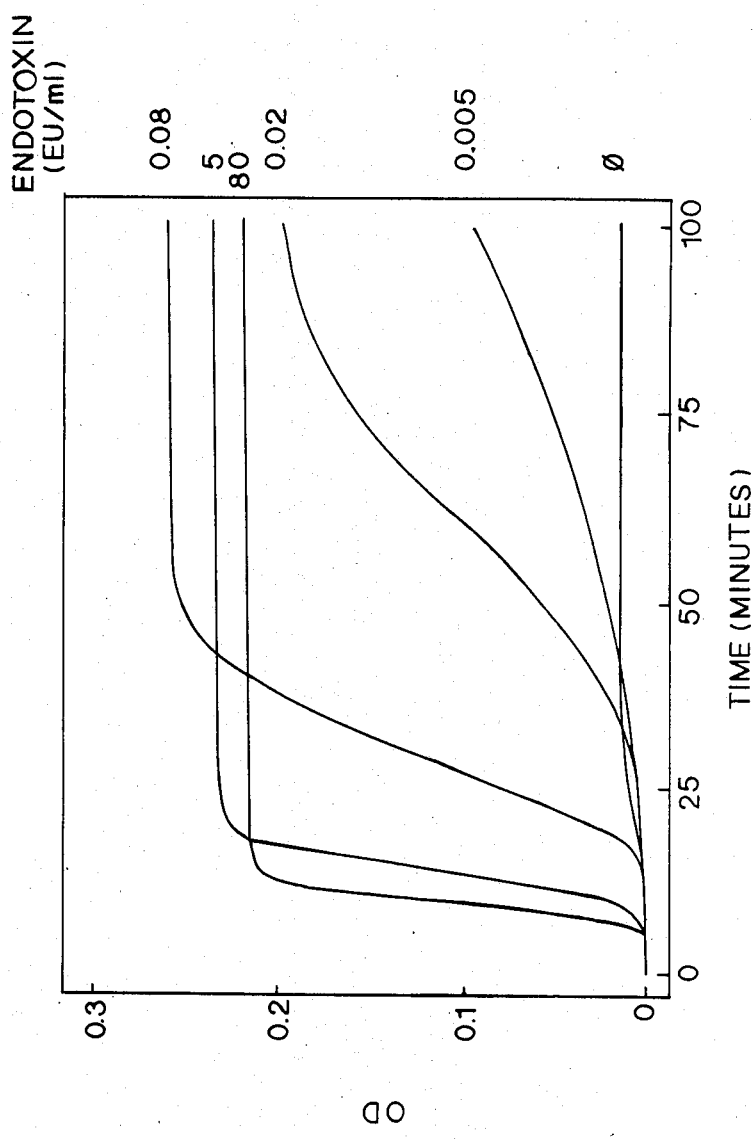
FIG. 1 shows characteristic reaction kinetics (optical density vs. time). The effect of the amount of endotoxin in the reaction mixture in regard to the variation in the time of onset and to the maximal increase in optical density can be seen.
Figure 2:
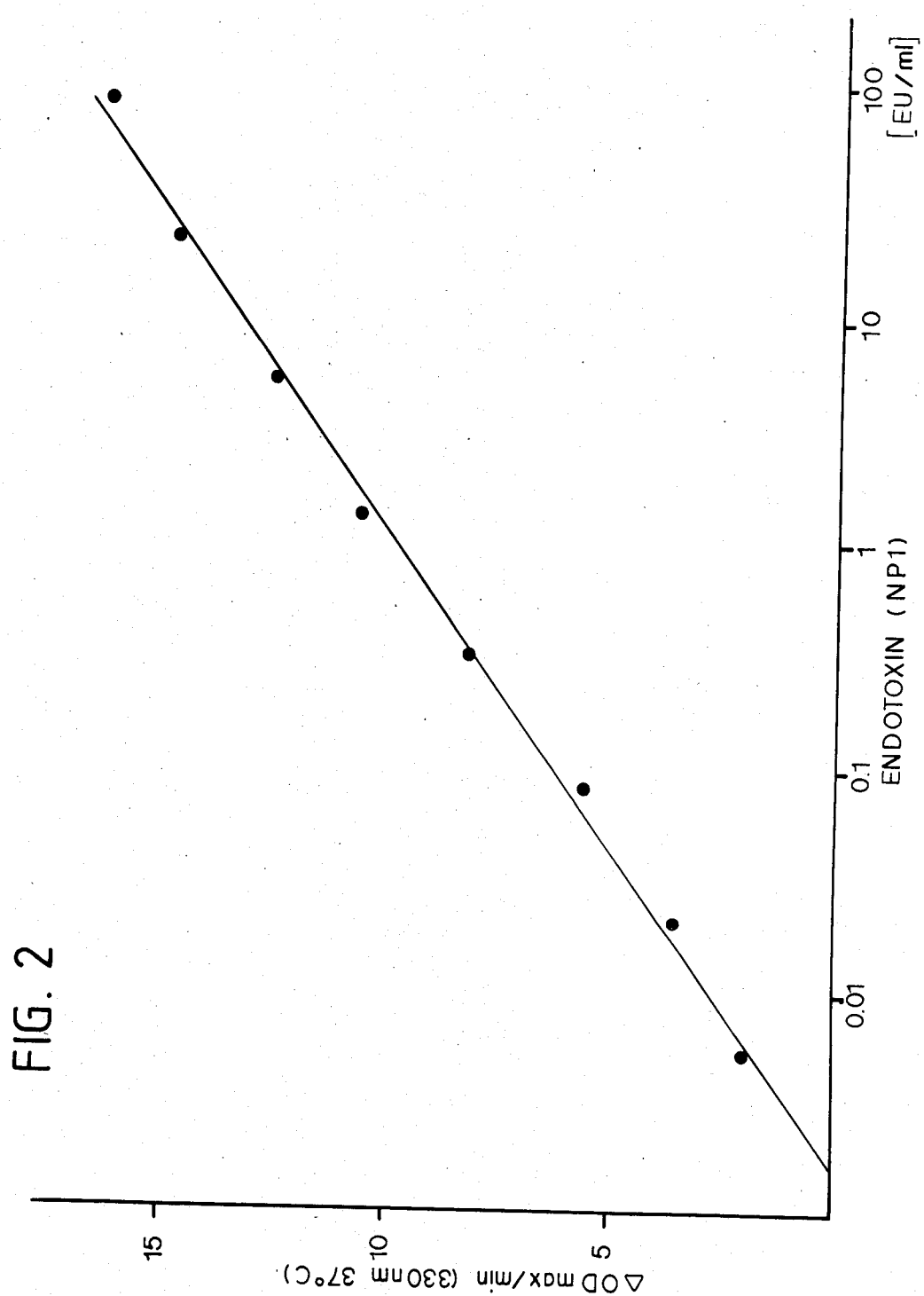
FIG. 2 shows a characteristic endotoxin standard curve in water (maximal increase in optical density per minute ($\Delta OD_{max}/\min$) derived from the reaction kinetics (FIG. 1)). Using the $\Delta OD_{max}/\min$ as a parameter results in a remarkably wide linear range of the standard curve from lower than 0.01 EU/ml up to higher than 100 EU/ml (1 EU=100 pg of Novopyrexal NP1).
Figure 3:
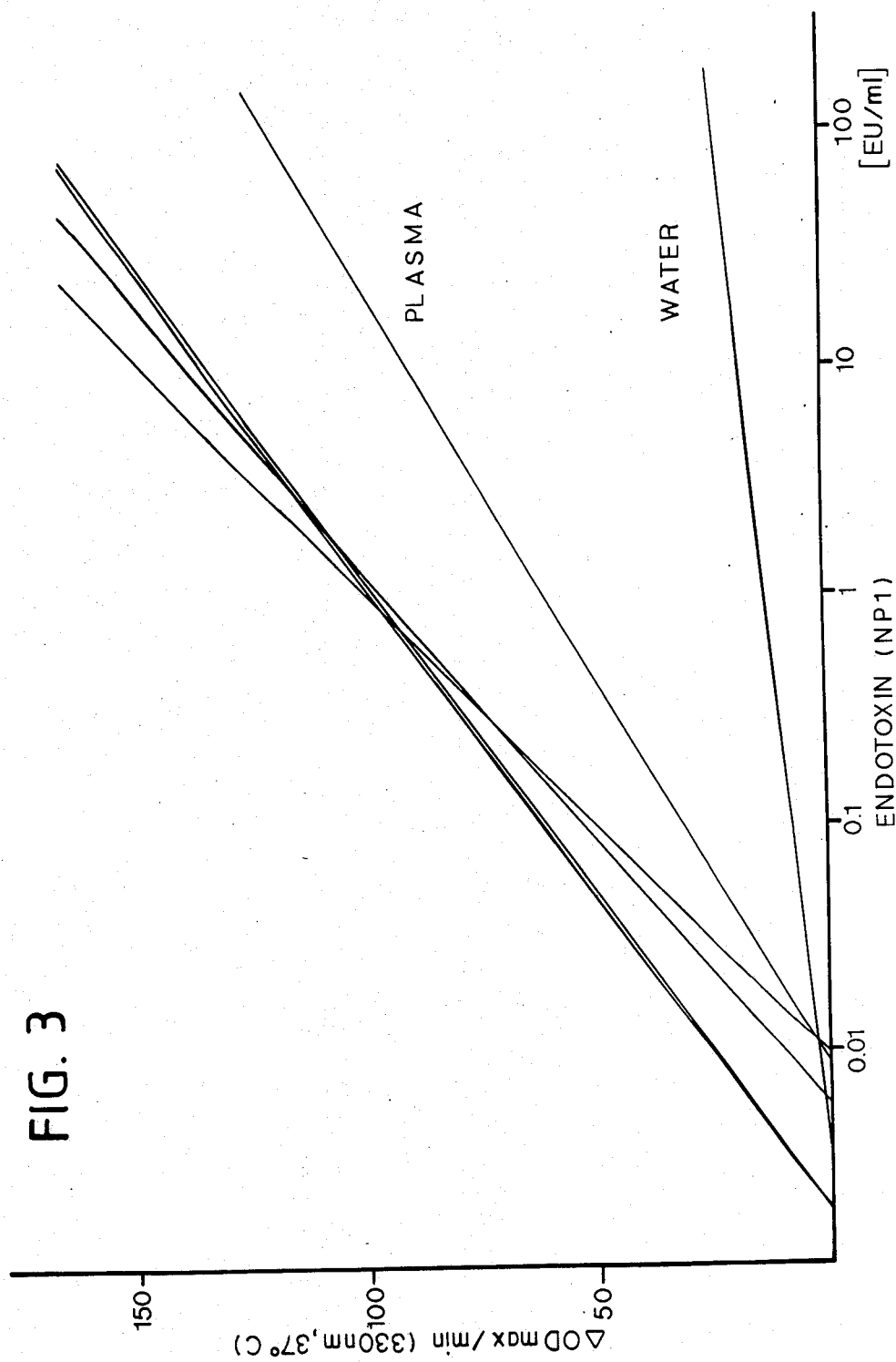

FIG. 3 shows endotoxin standard curves obtained in water and different plasma samples from healthy donors not containing endotoxin per se. The curves measured in heated plasma reveal the interference in the sense of an enhancement and vary considerably indicating the great individual differences of plasma-related interferences with the LAL-endotoxin reaction. Thus, it is not possible to read measurements of individual plasma samples from a standard curve obtained in water or for example in a pooled plasma.

Figure 4:
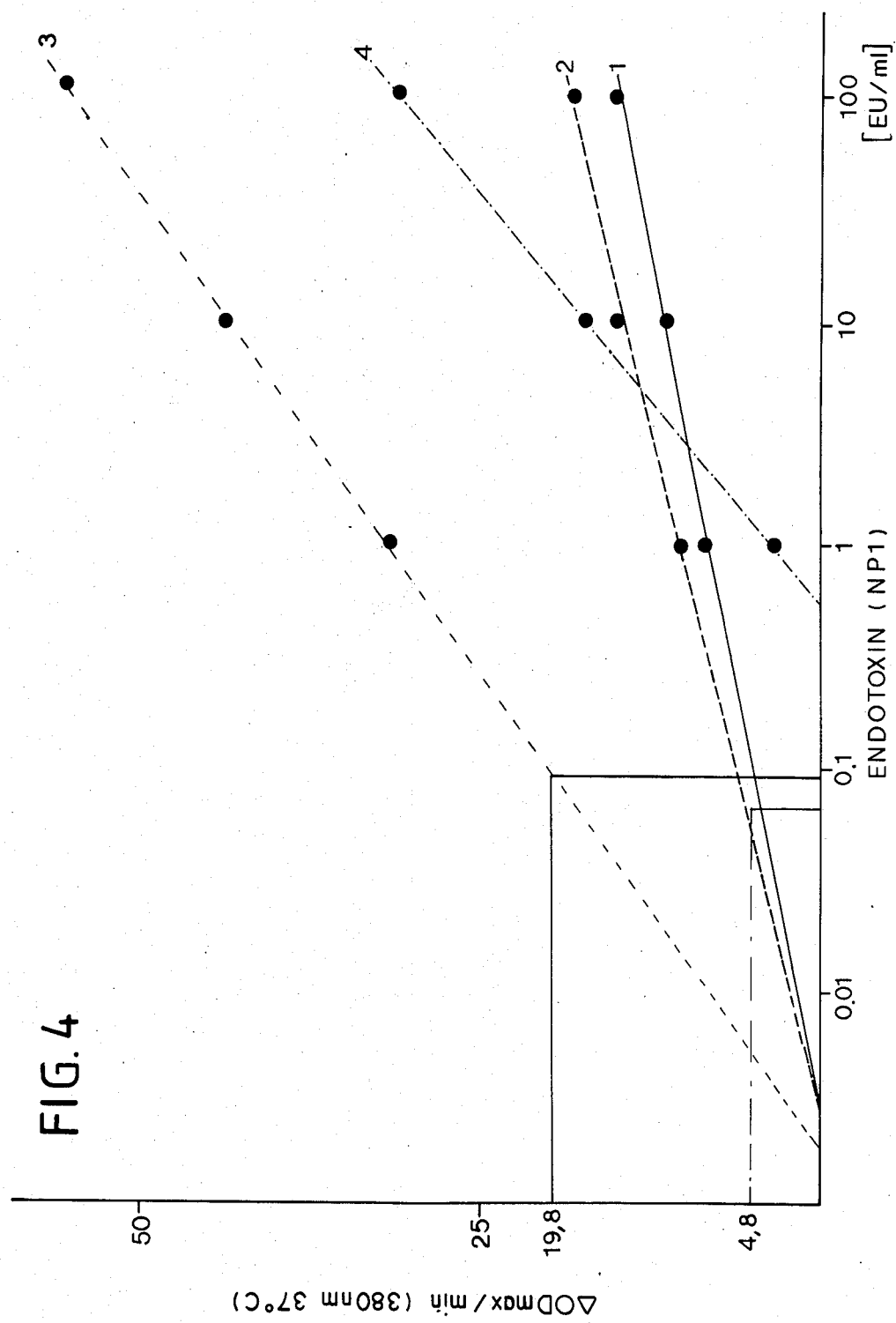

FIG. 4 shows the application of the method of internal standardization in 1. pyrogen-free water, 2. cerebrospinal fluid (CSF), 3. heated plasma, and 4. unheated plasma. By adding defined high amounts of endotoxin to each sample an individual standard curve for every sample is obtained. This individual standard curve is then used to read a measurement of the sample without additional endotoxin. For the definition of the individual sample internal standard curves endotoxin spikes of 100 EU/ml, 10 EU/ml and 1.0 EU/ml are used. These are high enough compared to the expected endotoxin contents of the samples.

In curve 4 (unheated plasma) the effect of the endotoxin neutralizing capacity can be seen. Up to about 0.6 EU/ml of added endotoxin no reaction is detectable.

The measured values and the results calculated from these for the Examples 1 through 4 of FIG. 4 are summarized in Table 1.

What is claimed is:

1. A method for determining endotoxin concentrations in a sample in spite of interfering factors, comprising:

adding known amounts of endotoxin to at least two substantially identical preparations of a sample, each of said amounts of endotoxin being different and being at least ten times the expected amount of endotoxin to be determined in the sample;

measuring the endotoxin concentrations in the samples to which endotoxin has been added using a kinetic method;

determining a regression line as a reference curve from the measured concentrations; and, determining the endotoxin concentration of the sample to which no endotoxin has been added from the regression line.

2. The method of claim 1, further comprising determining the effect of interfering factors and endotoxin neutralization capacity of a sample from the slope and position of the regression line in comparison to a regression line obtained from water or a standard solution.

3. The method of claim 1 wherein endotoxin concentration is determined by adding a chromogenic substrate and measuring at least one of turbidity and color absorption.

4. The method of claim 2, wherein endotoxin concentration is determined by adding a chromogenic substrate and measuring at least one of turbidity and color absorption.

* * * * *